United States Patent [19]
Lordo et al.

[11] Patent Number: 5,947,115
[45] Date of Patent: Sep. 7, 1999

[54] GAS FLOW PRESSURE FILTER

[75] Inventors: Richard J. Lordo, West Deer; John H. Fiore, Monroeville, both of Pa.

[73] Assignee: Respironics, Inc., Pittsburgh, Pa.

[21] Appl. No.: 08/909,118

[22] Filed: Aug. 11, 1997

Related U.S. Application Data

[63] Continuation-in-part of application No. 08/655,403, May 30, 1996, Pat. No. 5,655,522, which is a continuation of application No. 08/484,526, Jun. 7, 1995, Pat. No. 5,537,997, which is a continuation-in-part of application No. 08/378,467, Jan. 26, 1995, Pat. No. 5,540,219.

[51] Int. Cl.⁶ .................................................. A61M 15/00
[52] U.S. Cl. ............................... 128/200.24; 128/203.24; 128/912
[58] Field of Search .................. 128/200.24, 202.16, 128/202.27, 203.24, 203.28, 204.28, 205.14, 912; 138/28

[56] References Cited

U.S. PATENT DOCUMENTS

| | | | |
|---|---|---|---|
| 435,927 | 9/1890 | Ginty | 138/28 |
| 2,448,118 | 8/1948 | Pellettere | 138/28 |
| 2,737,178 | 3/1956 | Fox | 128/204.28 |
| 3,005,453 | 10/1961 | Wellenstein et al. | 128/204.28 |
| 3,822,725 | 7/1974 | Zirps | 138/28 |
| 3,976,064 | 8/1976 | Wood et al. | 128/204.28 |
| 4,364,384 | 12/1982 | Warncke et al. | 128/204.28 |
| 4,409,977 | 10/1983 | Bisera et al. | 128/205.14 |
| 4,655,213 | 4/1987 | Rapoport et al. | 128/205.25 |
| 4,686,999 | 8/1987 | Snyder | 128/716 |
| 4,773,411 | 9/1988 | Downs | 128/204.18 |
| 4,807,616 | 2/1989 | Adahan | 128/204.21 |
| 4,821,712 | 4/1989 | Gossett | 128/204.28 |
| 5,005,570 | 4/1991 | Perkins | 128/204.23 |
| 5,117,819 | 6/1992 | Servidio et al. | 128/204.18 |
| 5,148,802 | 9/1992 | Sanders et al. | 128/204.18 |
| 5,199,424 | 4/1993 | Sullivan et al. | 128/204.18 |
| 5,231,979 | 8/1993 | Rose et al. | 128/204.14 |
| 5,245,995 | 9/1993 | Sullivan et al. | 128/204.23 |
| 5,335,654 | 8/1994 | Rapoport | 128/204.23 |
| 5,584,289 | 12/1996 | Wise | 128/205.24 |
| 5,655,522 | 8/1997 | Mechlenburg et al. | 128/204.23 |
| 5,678,540 | 10/1997 | Kock et al. | 128/205.14 |

FOREIGN PATENT DOCUMENTS

WO 8810108  12/1988  WIPO.

OTHER PUBLICATIONS

Healthdyne Technologies' product brochure for "Tranquility Plus," undated.
Respironics, Inc. product brochure for "Humidifier" 1991.

*Primary Examiner*—Aaron J. Lewis
*Attorney, Agent, or Firm*—Reed, Smith, Shaw & McClay LLP

[57] ABSTRACT

Apparatus for delivering pressurized gas to the airway of a patient including: a gas flow generator for providing a flow of gas, a breathing appliance for sealingly communicating with the airway of the patient, and a conduit for delivery of the gas flow to the airway of the patient, the conduit having a first end connected to the gas flow generator and a second end connected to the breathing appliance. The apparatus further includes at least one sensor in fluid communication with the conduit and located substantially at the gas flow generator for detecting conditions corresponding to breathing patterns of the patient and generating signals corresponding to the conditions, and an information processor for receiving the signals and for controlling the output of the gas flow generator responsive to the signals. The apparatus further includes a gas flow pressure filter comprising a compliant chamber to reduce unwanted pressure fluctuations in the circuit to allow for the detection of desired signals, such as snore sounds.

24 Claims, 11 Drawing Sheets

GAS FLOW PRESSURE FILTER

This application is a continuation-in-part of application Ser. No. 08/655,403, filed on May 30, 1996, now U.S. Pat. No. 5,655,522 which is a continuation of application Ser. No. 08/484,526, filed on Jun. 7, 1995, which is now U.S. Pat. No. 5,537,997 which is a continuation-in-part of application Ser. No. 08/378,467, filed on Jan. 26, 1995 now U.S. Pat. No. 5,540,219.

FIELD OF THE INVENTION

The present invention relates generally to methodology and apparatus for treatment of sleep apnea and, more particularly, to mono-level, bi-level and variable positive airway pressure apparatus.

BACKGROUND OF THE INVENTION

The sleep apnea syndrome afflicts an estimated 1% to 5% of the general population and is due to episodic upper airway obstruction during sleep. Those afflicted with sleep apnea experience sleep fragmentation and intermittent, complete or nearly complete cessation of ventilation during sleep with potentially severe degrees of oxyhemoglobin desaturation. These features may be translated clinically into extreme daytime sleepiness, cardiac arrhythmias, pulmonary-artery hypertension, congestive heart failure and/or cognitive dysfunction. Other sequelae of sleep apnea include right ventricular dysfunction with cor pulmonale, carbon dioxide retention during wakefulness as well as during sleep, and continuous reduced arterial oxygen tension. Hypersomnolent sleep apnea patients may be at risk for excessive mortality from these factors as well as by an elevated risk for accidents while driving and/or operating potentially dangerous equipment.

Although details of the pathogenesis of upper airway obstruction in sleep apnea patients have not been fully defined, it is generally accepted that the mechanism includes either anatomic or functional abnormalities of the upper airway which result in increased air flow resistance. Such abnormalities may include narrowing of the upper airway due to suction forces evolved during inspiration, the effect of gravity pulling the tongue back to oppose the pharyngeal wall, and/or insufficient muscle tone in the upper airway dilator muscles. It has also been hypothesized that a mechanism responsible for the known association between obesity and sleep apnea is excessive soft tissue in the anterior and lateral neck which applies sufficient pressure on internal structures to narrow the airway.

The treatment of sleep apnea has included such surgical interventions as uvulopalatopharyngoplasty, gastric surgery for obesity, and maxillo-facial reconstruction. Another mode of surgical intervention used in the treatment of sleep apnea is tracheostomy. These treatments constitute major undertakings with considerable risk of postoperative morbidity if not mortality. Pharmacologic therapy has in general been disappointing, especially in patients with more than mild sleep apnea. In addition, side effects from the pharmacologic agents that have been used are frequent. Thus, medical practitioners continue to seek non-invasive modes of treatment for sleep apnea with high success rates and high patient compliance including, for example in cases relating to obesity, weight loss through a regimen of exercise and regulated diet.

Recent work in the treatment of sleep apnea has included the use of continuous positive airway pressure (CPAP) to maintain the airway of the patient in a continuously open state during sleep. For example, U.S. Pat. No. 4,655,213 discloses sleep apnea treatments based on continuous positive airway pressure applied within the airway of the patient.

An early mono-level CPAP apparatus is disclosed in U.S. Pat. No. 5,117,819 wherein the pressure is measured at the outlet of the blower so as to detect pressure changes caused by the patient's breathing. The arrangement is such that the control motor is regulated by the microprocessor to maintain the pressure at constant level regardless of whether the patient is inhaling or exhaling.

Also of interest is U.S. Pat. No. 4,773,411 which discloses a method and apparatus for ventilatory treatment characterized as airway pressure release ventilation and which provides a substantially constant elevated airway pressure with periodic short term reductions of the elevated airway pressure to a pressure magnitude no less than ambient atmospheric pressure.

U.S. Pat. Nos. 5,245,995 5,199,424, and 5,335,654, and published PCT Application No. WO 88/10108 describes a CPAP apparatus which includes a feedback/diagnostic system for controlling the output pressure of a variable pressure air source whereby output pressure from the air source is increased in response to detection of sound indicative of snoring. The apparatus disclosed in these documents further include means for reducing the CPAP level to a minimum level to maintain unobstructed breathing in the absence of breathing patterns indicative of obstructed breathing, e.g., snoring.

Bi-level positive airway therapy for treatment of sleep apnea and related disorders is taught in U.S. Pat. No. 5,148,802. In bi-level therapy, pressure is applied alternately at relatively higher and lower prescription pressure levels within the airway of the patient so that the pressure-induced patent force applied to the patients airway is alternately a larger and a smaller magnitude force. The higher and lower magnitude positive prescription pressure levels, which will be hereinafter referred to by the acronyms IPAP (inspiratory positive airway pressure) and EPAP (expiratory positive airway pressure), may be initiated by spontaneous patient respiration, apparatus preprogramming, or both, with the higher magnitude pressure (IPAP) being applied during inspiration and the lower magnitude pressure (EPAP) being applied during expiration. This method of treatment may descriptively be referred to as bi-level therapy. In bi-level therapy, it is EPAP which has the greater impact upon patient comfort. Hence, the treating physician must be cognizant of maintaining EPAP as low as is reasonably possible to maintain sufficient pharyngeal patency during expiration, while optimizing user tolerance and efficiency of the therapy.

Both inspiratory and expiratory air flow resistances in the airway are elevated during sleep preceding the onset of apnea, although the airway flow resistance may be less during expiration than during inspiration. Thus it follows that the bi-level therapy as characterized above should be sufficient to maintain pharyngeal patency during expiration even though the pressure applied during expiration is generally not as high as that needed to maintain pharyngeal patency during inspiration. In addition, some patients may have increased upper airway resistance primarily during inspiration with resulting adverse physiologic consequences. Thus, depending upon a particular patient's breathing requirements, elevated pressure may be applied only during inhalation thus eliminating the need for global (inhalation and exhalation) increases in airway pressure. The relatively lower pressure applied during expiration may in some cases approach or equal ambient pressure. The lower pressure applied in the airway during expiration enhances patient tolerance by alleviating some of the uncomfortable sensations normally associated with mono-level CPAP.

Although mono-level, bi-level and variable positive airway pressure therapy has been found to be very effective and generally well accepted, they suffer from some of the same limitations, although to a lesser degree, as do the surgery options; specifically, a significant proportion of sleep apnea patients do not tolerate positive airway pressure well. Thus, development of other viable non-invasive therapies and better versions of existing therapies has been a continuing objective in the art.

In this regard, even the more sophisticated CPAP apparatus heretofore known in the art, including those described in U.S. Pat. Nos. 5,245,995 5,199,424, and 5,335,654, and published PCT Application No. WO 88/10108, suffer from certain operational disadvantages which stem from the structural relationships of their essential components.

More particularly, the CPAP apparatus disclosed in U.S. Pat. Nos. 5,245,995 5,199,424, and 5,335,654, and published PCT Application No. WO 88/10108 provide feedback/diagnostic systems including at least one sensor (typically an audio transducer such as a microphone) in communication with the patient's respiratory system. This sensor is located on or is connected to means (such as a breathing mask or nasal prongs) in sealed air communication with a patient's respiratory system. The sensor continuously senses the patient's breathing patterns and transmits signals indicative of those patterns to information processing means which control the motor speed of a blower. The breathing pattern signals can also be continuously monitored and/or recorded, thereby imparting to the apparatus a diagnostic as well as therapeutic capability.

The blower delivers pressurized air to the patient through a length of conduit and the breathing mask or nasal prongs. When the sensor detects breathing patterns indicative of obstructed breathing, e.g., snoring, it transmit signals corresponding to this condition to the information processing means which causes an increase in blower motor speed and, therefore, blower pressure output, until unobstructed breathing is eliminated. The system also includes logic whereby blower motor speed (and blower pressure output) is gradually decreased if unobstructed breathing patterns are detected over a preselected period of time. The purpose of this feature is to provide the patient with a pressure minimally sufficient to maintain airway patency during unobstructed breathing, thereby enhancing patient comfort and therapy compliance.

Despite the general effectiveness of these apparatus, however, the structural relationship of their feedback/diagnostic system with respect to the patient's breathing circuit (i.e., the blower, gas delivery conduit, and breathing mask or nasal prongs) results in an arrangement of lesser reliability than would otherwise be desirable.

For example, certain feedback/diagnostic systems utilize a breathing pattern sensor mounted on or connected to the breathing mask or nasal prongs. Such an arrangement requires a length of feedback conduit to be added to the patient's breathing circuit. The feedback conduit extends from the breathing patterns sensor at the mask to the blower.

Such an added feedback conduit renders the patient's breathing circuit cumbersome and increases the risk of entanglement of the feedback circuit. The arrangement also increases the risk of the feedback conduit becoming kinked or having the conduit accidentally disconnected from the breathing mask, either of which render the device inoperable. Such a feedback conduit also requires frequent cleaning because it is in contact with the patient's expired air.

An advantage exists, therefore, for an apparatus for delivering pressurized air to the airway of a patient which includes a feedback/diagnostic system of higher reliability and increased ease of use, whereby diagnostic accuracy and patient comfort and adherence to the therapy administered by the apparatus are optimized.

A problem associated with positive airway pressure devices is a lack of moisture in the air delivered by these devices has a drying effect on patient airways which causes the patient to have considerable discomfort and difficulty sleeping.

Humidifiers have been developed for use with CPAP devices to humidify the air supplied to the patient. In the type of system according to the present invention in which the sensor is situated generally at an end of the breathing circuit remote from the patient any type of accessory such as a humidifier may attenuate or absorb snore sound.

Humidifiers for use with CPAP apparatus are taught in U.S. Pat. Nos. 4,807,616 and 5,231,979. Other humidifiers of interest are manufactured by Respironics, Inc. of Murrysville, Pa. and Healthdyne Technologies. However, these humidifiers are for use with conventional CPAP apparatus and therefore are not configured to acoustically tune snoring sound as required for use with the unique sleep apnea treatment apparatus of the present invention.

An advantage exists, therefore, for a humidifier which is configured to acoustically tune the snoring sound received from a patient in order to set the resonant frequency of the snore sound.

In some instances, the gas flow generator supplying the pressurized gas may produce excessive pressure fluctuations. These pressure fluctuations are imposed on the fluid stream. The excessive pressure fluctuations hinder the ability to detect other pressure/flow fluctuations which may be of interest. Presently, complex signal processing techniques are used to extract the signals of interest and eliminate unwanted signals produced by excessive pressure fluctuations. These techniques are expensive, require long development times, and success is not guaranteed.

An advantage therefore exists for a cost-effective, efficient device for minimizing excessive pressure fluctuations, to provide smooth gas flow, and allow for the detection of desired signals.

SUMMARY OF THE INVENTION

The present invention contemplates a novel and improved method for treatment of sleep apnea as well as novel methodology and apparatus for carrying out such improved treatment method. The invention contemplates the treatment of sleep apnea through application of pressure at variance with ambient atmospheric pressure within the upper airway of the patient in a manner to promote patency of the airway to thereby relieve upper airway occlusion during sleep.

According to the invention, positive pressure may be applied at a substantially constant, "mono-level," patient-specific prescription pressure, at alternatively higher (IPAP) and lower (EPAP) "bi-level", pressures, or at variable pressures within the airway of the patient to maintain the requisite patent or "splint" force to sustain respiration during sleep periods.

In all embodiments considered to be within the scope of the instant invention, the apparatus for delivering pressurized breathing gas to the airway of a patient comprises a breathing gas flow generator, information processing means for controlling the output of the gas flow generator, and a length of flexible conduit connected at one end to the gas flow generator and at an opposite end to a patient interface means such as a breathing mask or nasal prongs. By controlling the output of the gas flow generator, the information processing means likewise controls the pressure of the breathing gas delivered to the patient through the flexible conduit and the patient interface means.

The apparatus further includes a novel feedback system which may impart both therapeutic as well as diagnostic capability to the apparatus. The feedback system includes at least one sensor means, such as a pressure or flow responsive transducer, located on, within or closely adjacent to the gas flow generator. The sensor means continuously senses the patient's breathing patterns and transmits signals indicative of those patterns to the information processing means. The apparatus may also include means whereby these signals can also be continuously monitored and/or recorded whereby the patient's specific breathing disorder may be diagnosed as well as treated by the apparatus.

Like the feedback/diagnostic systems known in the art, when the sensor detects breathing patterns indicative of obstructed breathing, it transmits signals corresponding to this condition to the information processing means. This means, which may be any suitable microprocessor or central processing unit (CPU), then causes the flow generator to increase its output which increases the air pressure delivered to the patient until obstructed breathing is no longer detected. The system also includes logic whereby the flow generator output is gradually decreased if unobstructed breathing patterns are detected over a preselected period of time. This feature serves to provide the patient with a pressure minimally sufficient to maintain airway patency during unobstructed breathing, thus enhancing patient comfort and therapy compliance.

Unlike other positive airway pressure apparatus equipped with feedback/diagnostic systems including a breathing patterns sensor located on or connected to the patient interface, the apparatus according to the present invention finds its breathing patterns sensor situated generally at the end of the breathing circuit remote from the patient. That is, the sensor is preferably located within, on or is connected closely adjacent to the outlet of the gas flow generator controller. Situating the breathing patterns sensor at this region of the breathing circuit realizes considerable improvements in apparatus performance characteristics and in particular sensor reliability and ease of use.

More specifically, by distancing the breathing patterns sensor from the patient interface (i.e., the breathing mask or nasal prongs), that portion of the along the patient's breathing circuit is eliminated, and only a relatively shorter feedback conduit is required and is provided. Consequently, the patient's breathing circuit is rendered considerably less cumbersome, the risk of entanglement is negatived, and any annoyance of the patient is minimized. The length of the shorter feedback conduit reduces, if not totally eliminates, the risk of being kinked or accidentally disconnected from the patient's breathing circuit. Additionally, frequent cleaning of the shorter feedback conduit is not required because it is not in direct contact with the patient's expired air. The shorter feedback conduit also reduces the materials cost for the system.

Admittedly, placement of the breathing patterns sensor substantially at or near the gas flow generator reduces the responsiveness of the apparatus to the patient's continually changing respiratory needs. However the reduction in responsiveness of the breathing patterns sensor is compensated for by resonant tuning of the system. That is, the frequency response of the patient's breathing circuit and internal tubing of the present system is acoustically tuned to optimally transmit sounds with frequency content which is known to be indicative of upper airway obstructions. Thus the tuned resonance is such that sounds (snores) with frequencies near the resonant frequency are amplified, thus boosting the signal-to-noise ratio (more accurately the ratio of snore noise to gas flow generator noise) back to the level which is comparable to that which has been obtained by sensing at the patient interface. As illustration, a patient's lack of demand or a reduced demand for inspiratory air often precedes, frequently by several seconds, by the onset of an audible snore or other pronounced physical manifestation indicative of obstructed breathing. The breathing pattern sensors typically must detect such salient occurrences before they register an obstructed breathing event. In such case, the sensor would transmit data to the CPU such that the CPU could step up the output of the flow generator well in advance of not only an apneic event but also prior to the characteristic audible snore patterns which normally precede such an event. Known breathing pattern sensors typically accomplish this while being located on or connected to the patient interface. The sensor of the present invention, on the other hand, may be an equally responsive pressure or flow transducer sensitive to pressure or flow variations of any selected magnitude and/or frequency, but located within, on or connected closely adjacent to the outlet of the gas flow generator.

In order to prevent drying of the breathing passage during the administration of pressurized air delivered by the flow generator of the present invention, it is desirable to use the present invention in combination with a humidifier. A problem associated with using a humidifier with the breathing pattern sensor of the present invention is the humidifier may attenuate or absorb snore sound. This and other problems have been solved by the humidifier in the present invention which includes a U-shaped accumulation chamber which is configured to acoustically tune the snoring sound received from a patient. The humidifier of the present invention is disclosed in more detail in U.S. Pat. No. 5,598,837, entitled "Passive Humidifier for Positive Airway Pressure Devices", the disclosure of which is hereby incorporated by reference.

The present invention further contemplates a cost-effective, efficient gas flow pressure filter for minimizing excessive pressure fluctuations. The gas flow pressure filter comprises a compliant chamber or bladder which expands and contracts in response to the pressure fluctuations created by the gas flow generator. The chamber absorbs energy from the fluid stream produced by the gas flow generator thereby minimizing downstream transmission of the pressure fluctuations created by the pressure/flow source.

It is desirable to use the gas flow pressure filter with the sleep apnea treatment apparatus disclosed herein to allow for the unhindered detection of snore sounds. However, it should be apparent that the gas flow pressure filter of the present invention has a wide range of applications and may be used in a wide range of positive airway pressure devices such as continuous or bi-level positive airway pressure devices. The gas flow pressure filter could be used to produce smoother gas flow signals to enhance the efficacy of many sensors, for example, the mass flow sensor used to trigger bi-level positive airway pressure devices.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
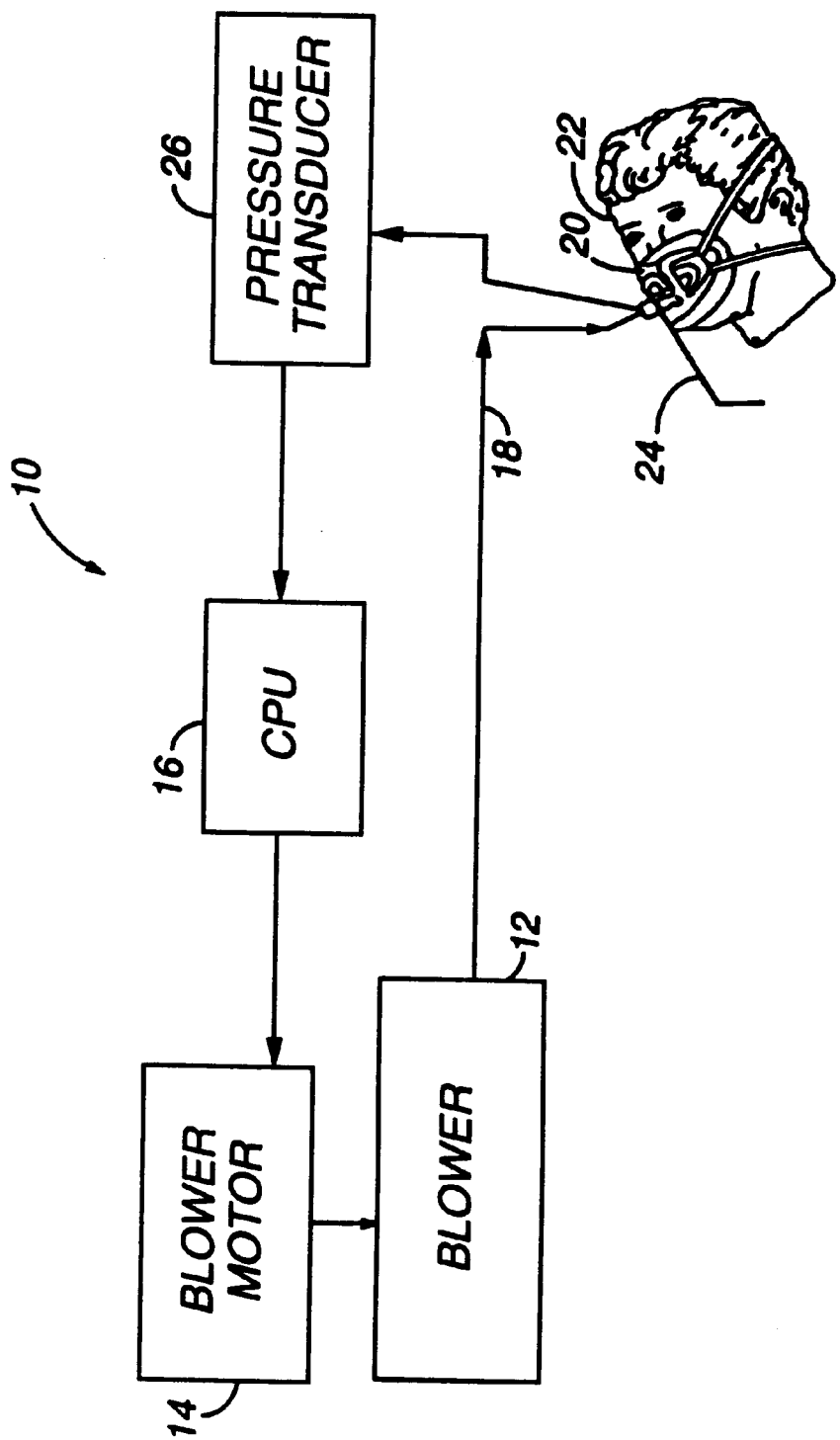
FIG. 1 is a functional block diagram of a prior art CPAP apparatus including a patient feedback/diagnostic system.

There is generally indicated at 10 in FIG. 1, in the form of a functional block diagram, a mono-level CPAP apparatus including a patient feedback/diagnostic system generally and schematically representative of the apparatus disclosed in U.S. Pat. Nos. 5,245,995 5,199,424, and 5,335,654, and published PCT Application No. WO 88/10108.

Apparatus 10 includes a blower 12 driven by an electric blower motor 14. The speed of motor 14 and thus the output of the blower 12 is controlled by an information processing means or central processing unit (CPU) 16. The output of the blower is connected by a suitable length of flexible gas delivery conduit means 18 to a patient interface means 20 such as, for example, nasal prongs or, as illustrated, a breathing mask which is in sealed air communication with the airway of a patient 22. If constructed as a breathing mask the patient interface means 20 may include suitable exhaust port means, schematically indicated at 24, for exhaust of breathing gas during expiration. Exhaust port means 24 may be a conventional non-rebreathing valve or one or more continuously open ports which impose a predetermined flow resistance against exhaust gas flow. Apparatus 10 also includes a suitable pressure transducer 26 located on or connected to the patient interface means 20. Typically, the pressure transducer 26 is an audio transducer or microphone.

When, for example, snoring sounds occur the pressure transducer detects the sounds and feeds corresponding electrical signals to the CPU 16 which, in turn, generates a flow generator motor control signal. Such signal increases the speed of the flow generator motor, thereby increasing output pressure supplied to the patient by the blower 12 through conduit means 18 and the patient interface means 20. The system may include suitable data storage and retrieval means (not illustrated) which may be connected to CPU 16 to enable medical personnel to monitor and/or record the patient's breathing patterns and thereby diagnose the patient's particular respiratory disorder and breathing requirements.

As snoring is caused by vibration of the soft palate, it is therefore indicative of an unstable airway and is a warning signal of the imminence of upper airway occlusion in patients that suffer obstructive sleep apnea. Snoring is itself undesirable not only as it is a disturbance to others but it is strongly believed to be connected with hypertension. If the resultant increase in system output pressure is sufficient to completely stabilize the airway, snoring will cease. If a further snoring sound is detected, the pressure is again incrementally increased. This process is repeated until the upper airway is stabilized and snoring ceases. Hence, the occurrence of obstructive apnea can be eliminated by application of minimum appropriate pressure at the time of use.

The feedback circuit also includes means to gradually decrease the output pressure if an extended period of snore-free breathing occurs in order to ensure that the pressure is maintained at a level as low as practicable to prevent the onset of apnea. This effect can be achieved, for example, by the CPU 16 which, in the absence of an electronic signal from the pressure transducer 26 indicative of snoring, continuously and gradually reduces the flow generator speed and output pressure over a period of time. If, however, a snore is detected by the first pressure transducer, the CPU will again act to incrementally increase the output of the flow generator. The feedback circuit of the present invention as will be discussed hereinafter in connection with FIG. 2 preferably includes similar means.

In use, a patient using apparatus 10 may connect himself to the apparatus and go to sleep. The output pressure is initially at a minimum operating value of, for example, approximately 3 cm $H_2O$ gauge pressure so as not to cause the previously mentioned operational problems of higher initial pressures. Not until some time after going to sleep, the patient's body relaxes, will the airway start to become unstable and the patient begin to snore. The pressure transducer 26 will then respond to a snore, or snore pattern, and via the CPU 16 increase the blower motor speed such that output pressure increases, for instance, by 1 cm $H_2O$ for each snore detected. The pressure can be increased relatively rapidly, if the patient's condition so requires, to a working pressure of the order of 8–20 cm, which is a typical requirement. Additionally, for ease of monitoring the variation over time a parameter such as pressure output can be recorded in some convenient retrievable form and medium (such as the aforesaid data storage and retrieval means) for periodic study by medical personnel.

If for example in the early stages of sleep some lesser output pressure will suffice, apparatus 10 will not increase the pressure until needed, that is, unless the airway becomes unstable and snoring commences, no increase in airway pressure is made. By continuously decreasing the output pressure at a rate of, for example, 1 cm $H_2O$ each 15 minutes in the absence of snoring, the pressure is never substantially greater than that required to prevent apnea.

The feedback circuit of FIG. 1 provides a system which adjusts apparatus output pressure according to variations in a patient's breathing requirements throughout an entire sleep period. Further, apparatus 10 will likewise accommodate variable output pressure requirements owing to general improvements or deteriorations in a patient's general physical condition as may occur over an extended period of time.

Despite the general effectiveness of apparatus 10, however, the structural relationship of its feedback/diagnostic system with respect to the patient's breathing circuit (i.e., the blower, gas delivery conduit, and breathing mask) results in an arrangement which can be cumbersome to use, inconvenient to maintain, and of lesser reliability.

The present invention overcomes deficiencies of currently available positive airway pressure apparatus such as apparatus 10 by proposing a novel feedback/diagnostic system which is adapted for use in mono-level, bi-level and variable output positive airway pressure apparatus. Although for brevity the invention will be described in detail as it may be adapted to mono-level positive airway pressure apparatus, it is further contemplated that the particulars of the present invention may also be gainfully adapted to equally preferred embodiments including bi-level and variable positive airway pressure apparatus, the general characteristics and functions of which are well known in the art. However, the particulars of the "bi-level", and "variable" positive airway pressure apparatus embodiments of the present invention will not be described at length. Consequently, it will nevertheless be understood that the presently proposed arrangement and operation of the feedback/diagnostic system components with respect to the breathing circuit will be substantially the same for a "bi-level", and "variable" positive airway pressure apparatus as those discussed hereinafter in connection with the "mono-level" embodiment of the invention.

Figure 2:
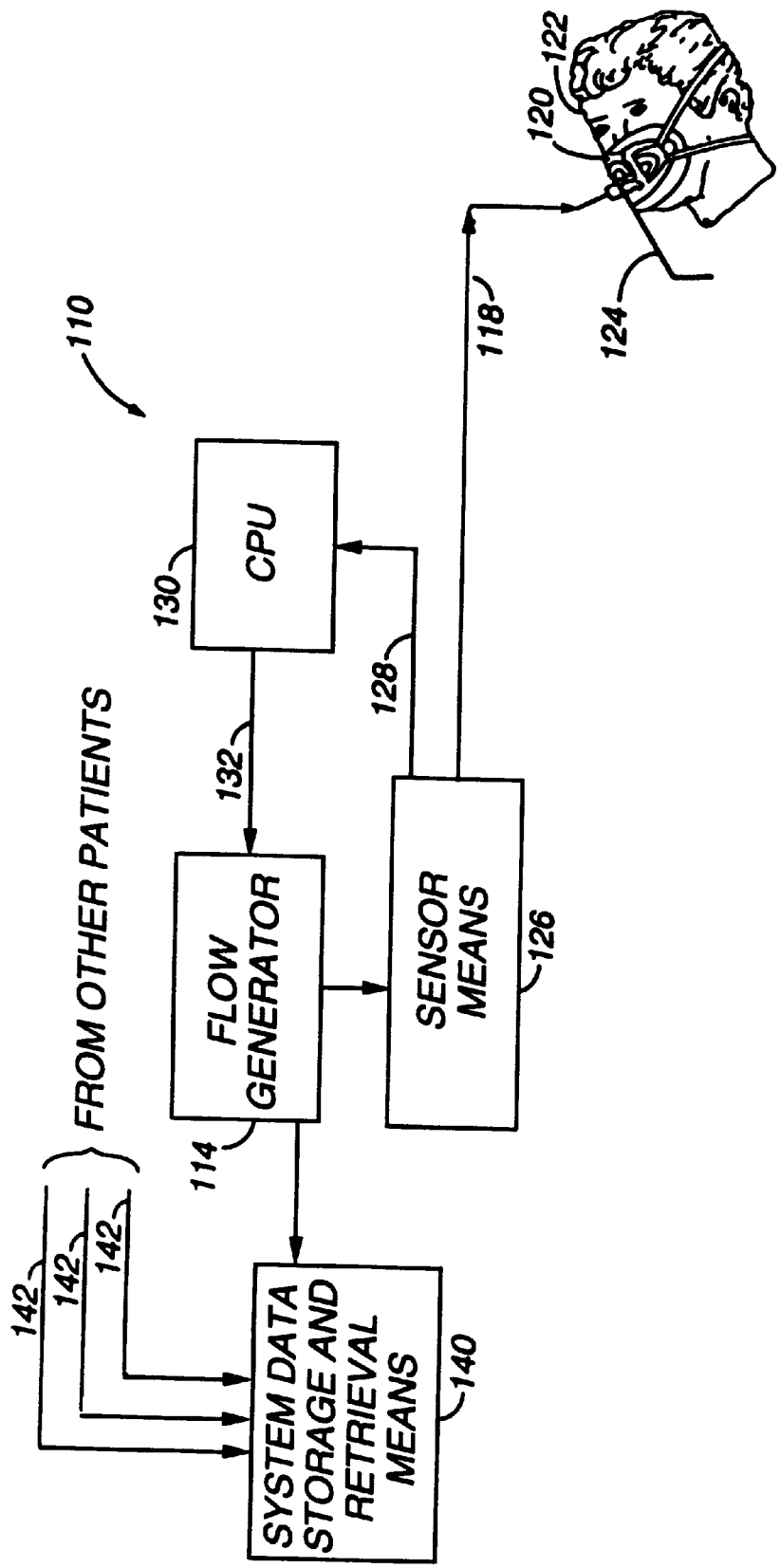
FIG. 2 is a functional block diagram showing a preferred embodiment of the present invention.

Referring to FIG. 2, there is illustrated in the form of a functional block diagram, an apparatus 110 representing perhaps the simplest of the presently preferred embodiments of the invention contemplated by applicants. Apparatus 110 includes a gas flow generator 114 (e.g., a blower) which receives breathing gas from any suitable source such as a pressurized bottle or the ambient atmosphere.

Located substantially at, i.e., within, on or connected closely adjacent to, the outlet of the gas flow generator 114 is a sensor means 126 in fluid communication with a flexible gas delivery conduit means 118. One end of conduit 118 is connected to the outlet of the gas flow generator 114. The conduit 118 communicates the output of the gas flow generator 114 to a patient interface means or breathing appliance 120 that is connected to the opposite end of the conduit 118. The patient interface means 120 may be a mask of any suitable known construction which is worn by patient 122 and is in sealed communication with the patient's airway. The patient interface means 120 may preferably be a nasal mask or a full face mask as illustrated and hereinafter referred. Other breathing appliances which may be used in lieu of a mask may include nasal cannulae, an endotracheal tube, or any other suitable appliance for interfacing between a source of breathing gas and a patient.

The mask 120 includes suitable exhaust port means, schematically indicated at 124, for exhaust of breathing gases during expiration. Exhaust port means 124 preferably is a continuously open port provided in the mask 120 or a non-rebreathing valve (NRV) situated closely adjacent the mask in conduit 118. The exhaust port means imposes a suitable flow resistance upon exhaust gas flow to permit an information processing means or central processing unit (CPU) 130, which receives signals generated by sensor means 126 as indicated at 128, to control the output of the gas flow generator in a manner to be described at greater length hereinafter.

The exhaust port means 124 may be of sufficient cross-sectional flow area to sustain a continuous exhaust flow of approximately 15 liters per minute. The flow via exhaust port means 124 is one component, and typically the major component of the overall system leakage, which is an important parameter of system operation.

Sensor means 126 preferably comprises at least one suitable pressure or flow transducer which continuously detects pressure or flow discharge substantially at the outlet of the gas flow generator, which pressure or flow reflects the patient's breathing patterns. Concurrently, the sensor means 126 generates output signals 128 corresponding to the continuously detected gas pressure or flow from the gas flow generator 114 and transmits these signals to a pressure or flow signal conditioning circuit of the CPU 130 for derivation of a signal proportional to the instantaneous pressure or flow rate of breathing gas within conduit 118. Such flow or pressure signal conditioning circuit may for example be of the type described in U.S. Pat. No. 5,148,802, the disclosure of which is incorporated herein by reference.

Depending upon the characteristics of the conditioned flow or pressure signal, the CPU may generate a command signal 132 to either increase or decrease the output of the gas flow generator 114, e.g., to increase or decrease the speed of an electric motor (not illustrated) thereof. The gas flow generator 114, sensor means 126 and CPU 130 thus comprise a feedback circuit or system capable of continuously and automatically controlling the breathing pressure supplied to the patient's airway responsive to the patient's respiratory requirements as dictated by the patient's breathing patterns.

Like the feedback/diagnostic systems known in the art, when the sensor means 126 detects breathing patterns indicative of obstructed breathing, it transmits signals corresponding to this condition to the CPU 130. The CPU then causes the gas flow generator 114 to increase its output which increases the air pressure delivered to the patient until obstructed breathing is no longer detected. The system also includes means such as appropriate logic programmed into the CPU whereby the gas flow generator output is gradually decreased if unobstructed breathing patterns are detected over a preselected period of time. This feature serves to provide the patient with a pressure minimally sufficient to maintain airway patency during unobstructed breathing, thus enhancing patient comfort and therapy compliance.

In many respects, therefore, the feedback circuit of the present invention performs similarly to the feedback circuits disclosed in previously discussed U.S. Pat. Nos. 5,245,995 and 5,199,424 and published PCT Application No. WO 88/10108. However, by situating the sensor means 126 proximate the outlet of the gas flow generator rather than proximate the patient interface means 120 many significant benefits in apparatus performance are realized, which translate into increased patient comfort and therapy compliance.

Admittedly, placement of the breathing patterns sensor substantially at or near the gas flow generator reduces the responsiveness of the apparatus to the patient's continually changing respiratory needs. However the reduction in responsiveness of the breathing patterns sensor is compensated for by resonant tuning of the system. That is, the frequency response of the patient's breathing circuit and internal tubing of the present system is acoustically tuned to optimally transmit sounds with frequency content which is known to be indicative or upper airway obstructions. Thus the tuned resonance is such that sounds with frequencies near the resonant frequency (snores) are amplified, thus boosting the signal-to-noise ratio (more accurately the ratio of snore noise to gas flow generator noise) back to the level which is comparable to that which has been obtained by sensing at the patient interface. As illustration, a patient's lack of demand or a reduced demand for inspiratory air often precedes, frequently by several seconds, the onset of an audible snore or other pronounced physical manifestation indicative of obstructed breathing. In such case, the sensor means would transmit data to the CPU 130 such that the CPU may step up the output of the gas flow generator 114 well in advance of not only an apneic event but also prior to the characteristic audible snore patterns which normally precede such an event. Known breathing pattern sensors typically accomplish this while being located on or connected to the patient interface. The sensor of the present invention, on the other hand, may be an equally responsive pressure or flow transducer sensitive to pressure or flow variations of any selected magnitude and/or frequency, but located within, on or connected closely adjacent to the outlet of the gas flow generator.

In addition to its accurate and responsive feedback capability, the feedback circuit of apparatus 110, by virtue of the strategic placement of sensor means 126, also affords medical personnel the opportunity to monitor and/or record the patient's breathing activity with high precision. With this capability, the medical personnel may confidently diagnose the patient's particular breathing disorder, prescribe the appropriate therapy, and monitor the patient's progress while undergoing treatment using apparatus 110. In this regard, such monitoring and/or recording may be achieved by system data storage and retrieval means 140.

System data storage and retrieval means 140 may within the scope of the present invention comprise any suitable computer memory into which information can be written and from which information can be read. Representative, although not limitative, embodiments of the system data storage and retrieval means may therefore include a random access memory (RAM), magnetic tapes or magnetic disks which may be incorporated into a stand-alone personal computer, mainframe computer, or the like (not illustrated).

System data storage and retrieval means 140 may be configured to record output data from gas flow generator 114 and/or, as indicated, it may compile data from one or more data input lines 142 which communicate data transmitted by other sensors or monitors (not shown) which are operatively connected to other patients in a manner known to those skilled in the art.

Figure 3:
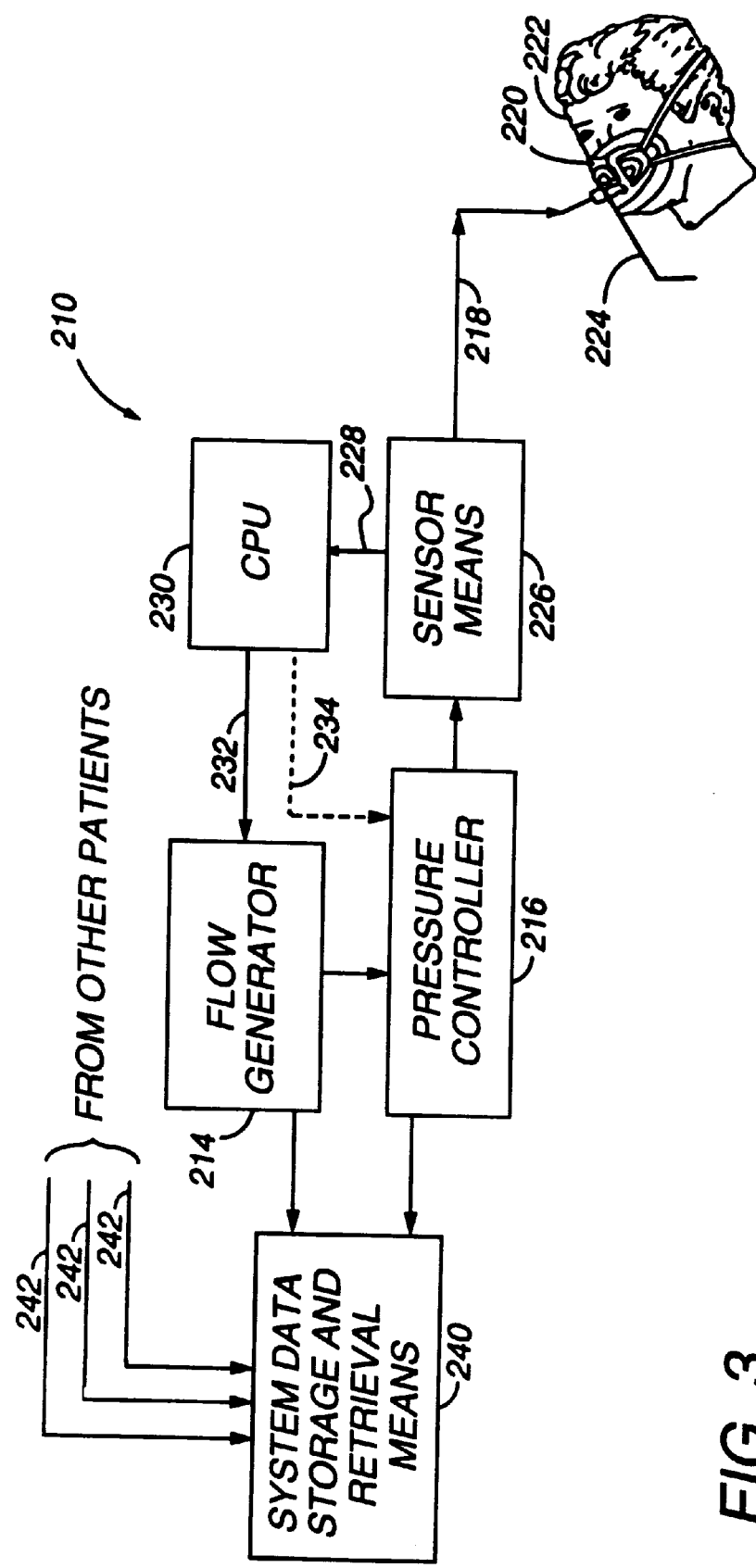
FIG. 3 is a functional block diagram of a further preferred embodiment of the present invention.

FIG. 3 reveals, in the form of a functional block diagram, an apparatus 210 for use in treatment of sleep apnea and related disorders that is constructed in accordance with a further preferred embodiment of the present invention. For brevity, only those elements of apparatus 210 which depart materially in structure and/or function from their counterpart elements in FIG. 2 will be described in detail where such description is necessary for a proper understanding of the invention. In other words, except where otherwise indicated, gas flow generator 214, conduit means 218, patient interface means 220, exhaust port means 224, sensor means 226, CPU 230 and system data storage and retrieval means 240 of FIG. 3 desirably are constructed as and function substantially identically to gas flow generator 114, conduit 118, patient interface means 120, exhaust port means 124, sensor means 126, CPU 130 and system data storage and retrieval means 140 discussed hereinabove in connection with FIG. 2.

The primary distinction between apparatus 210 and apparatus 110 is the presence of a pressure controller 216 which may be controlled separately from and in addition to the gas flow generator 214 by CPU 230.

The pressure controller 26 is thus operative to regulate, at least in part, the pressure of breathing gas within the conduit means 218 and thus within the airway of the patient 222. Pressure controller 216 is located preferably, although not necessarily, within or closely downstream of flow generator 214 and may take the form of an adjustable valve, the valve being adjustable to provide a constant or variable pressure drop across the valve for all flow rates and thus any desired pressure within conduit means 218.

Interposed in line with conduit means 218, downstream and substantially adjacent to pressure controller 216, is a suitable sensor means 226 such as a pressure or flow transducer which generates an output signal that is fed as indicated at 228 to a pressure or flow signal conditioning circuit of CPU 230 for derivation of a signal proportional to the instantaneous pressure or flow rate of breathing gas within conduit means 218 to the patient.

Depending upon the instantaneous pressure or flow condition detected by sensor means 226, which feeds a signal 228 corresponding to that condition to the CPU 230, the CPU may generate and transmit a command signal 232 to increase or decrease the output of the gas flow generator 214 in the manner discussed above in connection with the description of FIG. 2. Alternatively, or in addition to, command signal 232, the CPU may generate and transmit command signal 234 (shown in dashed line) to the pressure controller 216 to adjust the pressure drop produced thereby. In this way particularly sophisticated instantaneous pressure output patterns may be achieved to satisfy the demands of the patient on a breath-to-breath basis.

Furthermore, data storage and retrieval means 240 may be configured to compile input not only from the gas flow generator 214 and from the patient 222 via input lines 242, but also from the pressure controller 216 to provide the overseeing medical personnel an even more complete representation of the patient's respiratory activity.

Figure 4:
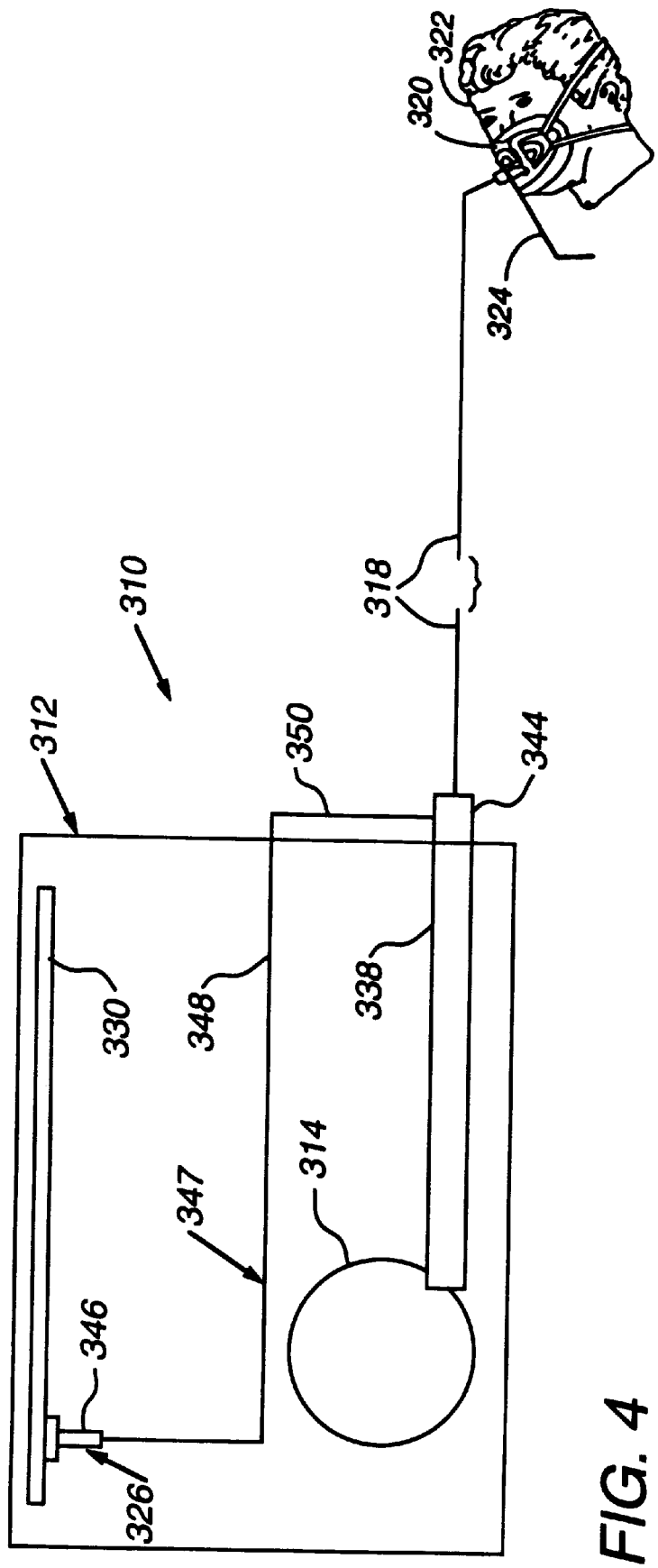
FIG. 4 is a view schematically illustrating a preferred embodiment of the present invention.

FIG. 4 schematically illustrates an arrangement wherein apparatus 310 includes a device 312 incorporating the flow generator 314, breathing patterns sensor means 326, a CPU or central processing unit 330 which includes a pressure controller (not illustrated). The flow generator 314 presents a bellows 338 terminating in a circuit coupler 344 presented externally of the device 312. A patient or first conduit means 318 has one end connected to the circuit coupler 344 and an opposite end connected to the patient interface means 320 which includes exhaust port means 324.

Unlike other positive airway pressure apparatus equipped with feedback/diagnostic systems including a breathing patterns sensor located on or connected to the patient interface, the apparatus 310 according to the present invention finds its breathing patterns sensor means 326 situated generally at the end of the breathing circuit remote from the patient 322. That is, the sensor 326 is preferably located within, on or is connected closely adjacent to the outlet of the gas flow generator 314. More specifically, the sensor means 326 comprises a pressure transducer 346 operably connected to the CPU 330. The sensor means 326 is in fluid communication with the patient or first conduit means 318 by means of sensor or second conduit 347. In accordance with the present invention, the sensor or second conduit means 347 comprises a internal conduit portion 348 disposed entirely within the device 312, and an external conduit portion 350 disposed exteriorly of the device 312. The sensor or second conduit means 347 has one end connected to the pressure transducer 346 and an opposite end connected to the patient or first conduit means 318 through the circuit coupler 344 and thus provide sound pressure communication between the pressure transducer 346 and the patient or first conduit means 318 through the circuit coupler 344. The arrangement is such that when the transmitted sound wave is close to the resonant frequency of the system, greatly amplified sound pressure will be transmitted from the mask 320 through the patient or first conduit means 318, the circuit coupler 344, and the sensor or second conduit means 347 to the pressure transducer 346. That is, the system responds like a harmonic oscillator with one degree of freedom.

By taking advantage of moving the sensor means 326 back to the device 312, the present invention provides system that is acoustically tuned to optimally transmit sounds in the frequency range of 20 to 120 Hz (the same range of sounds that are indicative of upper airway obstructions).

In apparatus, such as that illustrated in FIG. 4, the volume and entrance characteristics of the bellows 338, the blower 314, and the patient circuit 318 also affect the resonance properties in a complex manner.

Therefore the optimum lengths of the internal and external conduit portions 348, 350 are best verified empirically. This is achieved by placing a sound source at the patient mask 320, sweeping through the range of frequencies of interest, and measuring the output response of the pressure transducer 346. The lengths of the internal and external conduit portions 348, 350 are varied until the desired frequency response is achieved.

In one operative embodiment of the apparatus of FIG. 4, one-eighth inch inner diameter tubing is used as the internal and external conduit portions 348, 350. A length L of 40 inches of the internal and external conduit portions 348, 350 was found to provide the desired resonant frequency, w of 70 cycles per second. At that resonant frequency, the apparatus 310 is acoustically tuned to optimally transmit sounds in the target frequency range of 20 to 120 Hz—the primary frequency range of sounds that are indicative of upper airway obstruction. It should be understood, however, that the length L of the internal and external conduits 348, 350 will change with changes in the system elements. That is, the particular type of patient circuit 318, blower 314, bellows 338, circuit coupler 344, and pressure transducer 346 used in the system do determine the length L of the internal and external conduits 348, 350 that is required to produce the desired resonant frequency of 70 cycles per second. Likewise, it should be understood that the frequencies of sounds associated with upper airway obstructions are known to fall within a range of about 20 to 2,000 Hz. Therefore, other operative embodiments of the apparatus may be tuned by similar methods to resonant frequencies other than 70 Hz.

It should also be apparent that by distancing the breathing patterns sensor from the patient interface (i.e., the breathing mask or nasal prongs), the patient conduit means 318 is rendered considerably less cumbersome, the risk of entanglement is negatived, and the annoyance of the patient is minimized. The length of the shorter feedback conduit reduces, if not totally eliminates, the risk of being kinked or accidentally disconnected from the patient's breathing circuit. Additionally, frequent cleaning of the shorter feedback conduit is not required because it is not in direct contact with the patient's expired air. The shorter feedback conduit also reduces the materials cost for the system.

Figure 5:
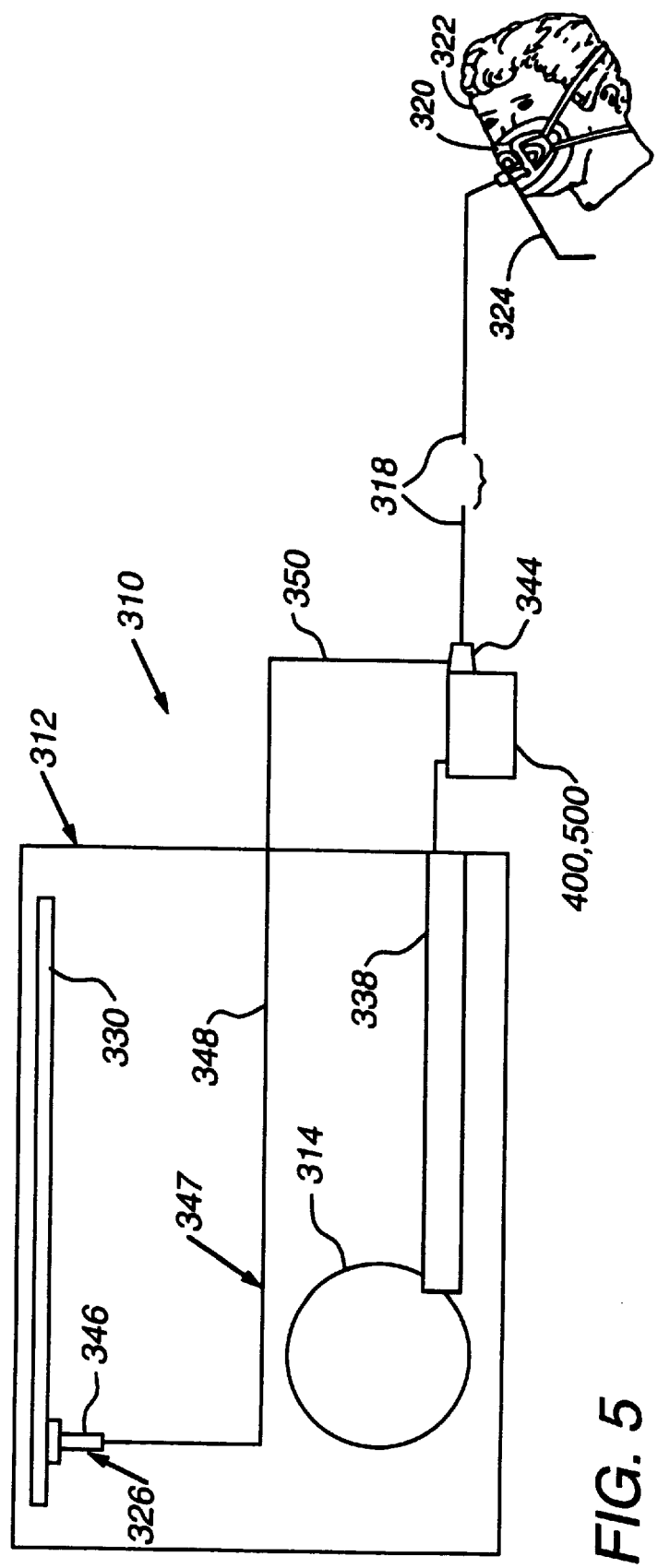
FIG. 5 is a view schematically illustrating the sleep apnea treatment apparatus of the present invention in use with a humidifier of the present invention.
Figure 6:
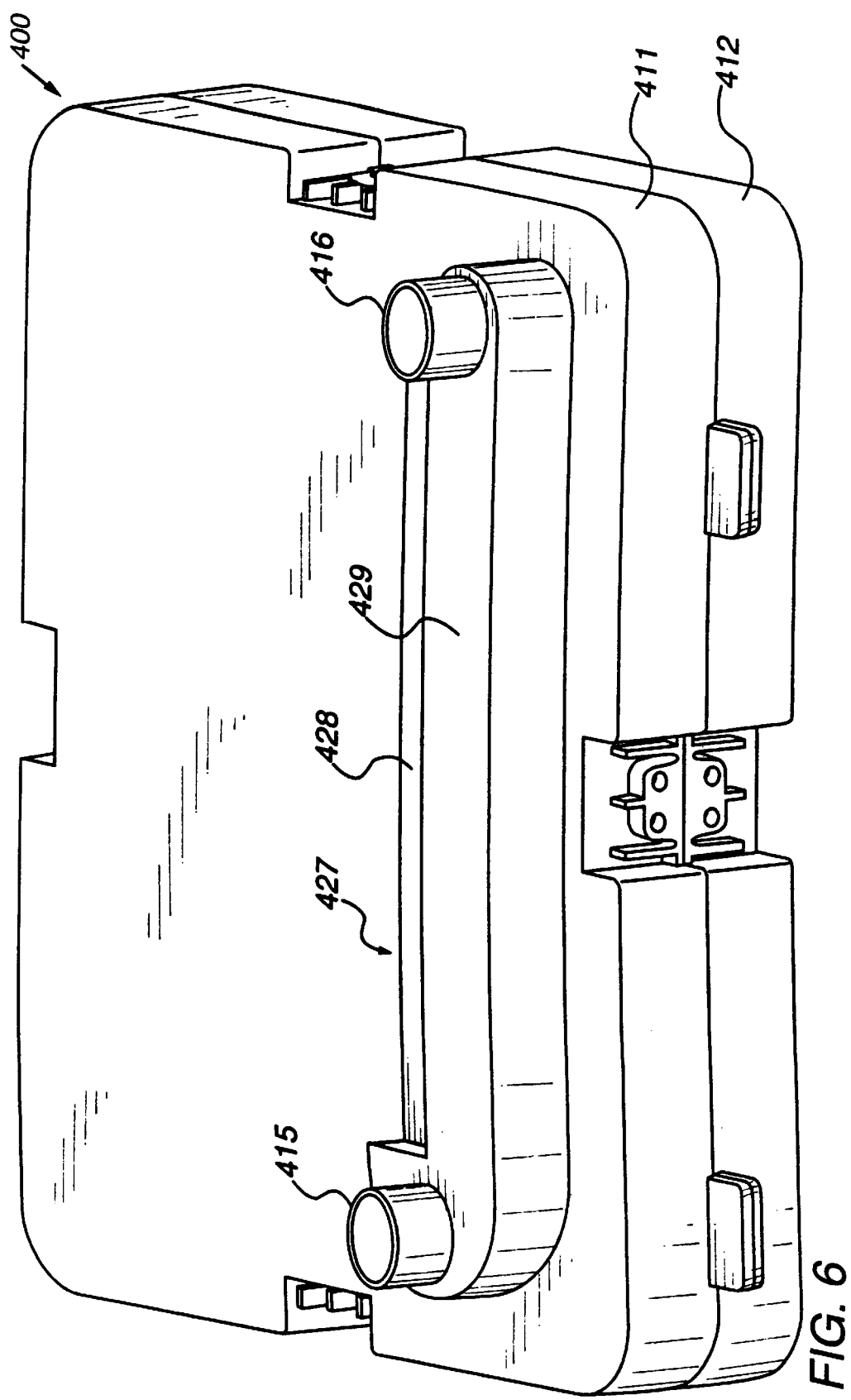
FIG. 6 is a perspective view of a humidifier of a first embodiment of the present invention showing a humidifier top and a humidifier base in assembled condition.
Figure 7:
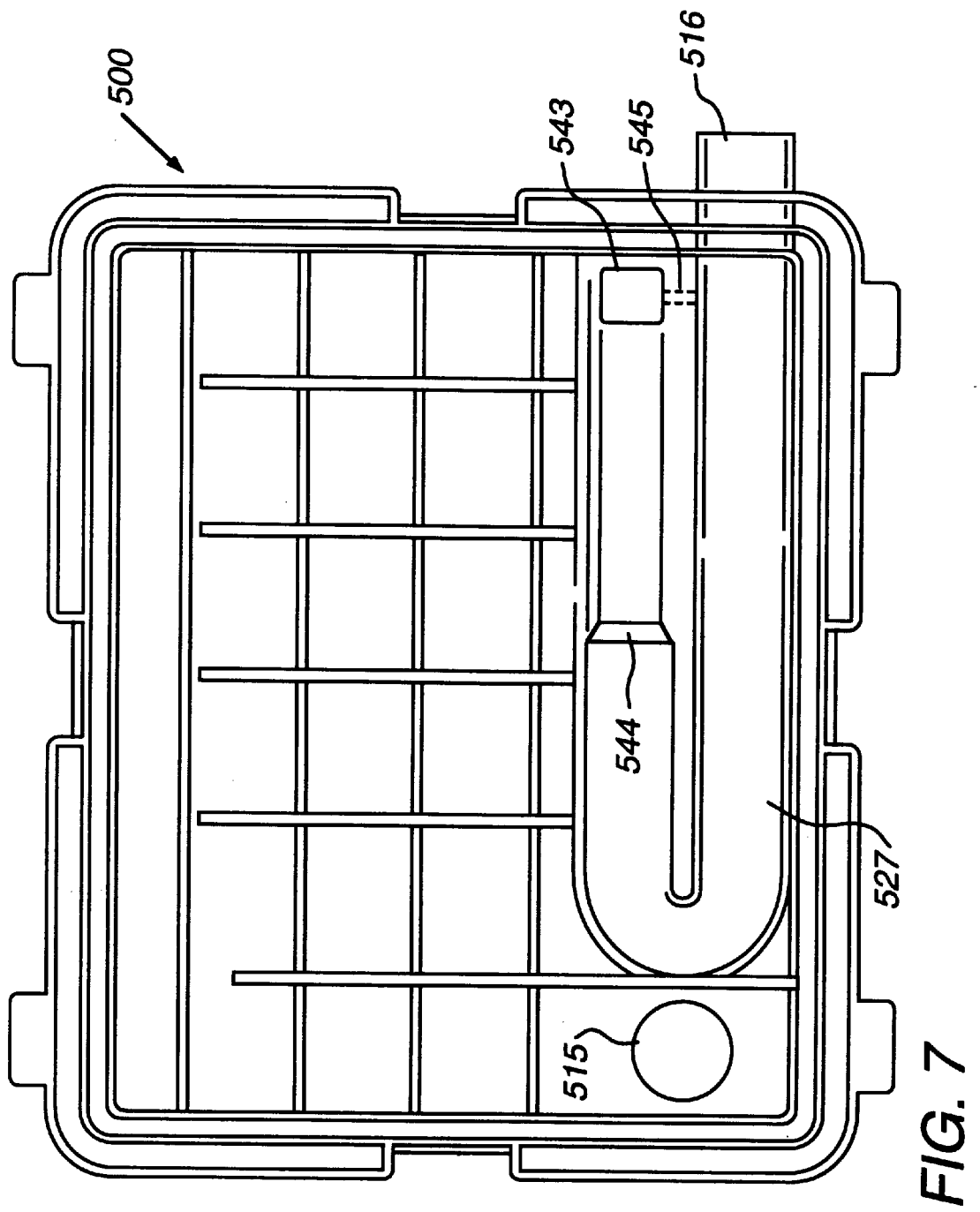
FIG. 7 is a plan view of a humidifier top of a presently preferred second embodiment viewed from the bottom.

Turning to FIGS. 5–7, a sleep apnea treatment apparatus according to the present invention is illustrated in combination with a humidifier of the present invention. When the apparatus 310 according to the present invention includes a humidifier 400 or 500, the circuit coupler 344 detaches from the gas flow generator device 312 and to an outlet 416 of the humidifier 400 or 500. An inlet 415 is then connected to the outlet of the gas flow generator device 312. Referring to FIG. 6, humidifier 400 has a U-shaped chamber 427 having a first leg 428 which directs air from the body of the humidifier and a second leg 429 which directs air towards the outlet 416. The U-shaped chamber 427 acoustically tunes the snoring sound received from a patient. In an alternative preferred embodiment illustrated in FIG. 7, humidifier 500 includes an inlet 516 and a U-shaped chamber 527 having a chamber inlet 543, a diameter transition portion 544 and a laterally extending outlet 515. The configuration of the U-shaped chamber 527 optimally transmits sound frequencies falling within a frequency range which is known to be associated with upper airway obstructions by setting the resonant frequency of the snore sound. The position of the diameter transition portion 544 controls the resonant frequency such that the resonant frequency of interest may be selected. Further included is a dissipation hole 54S between chamber inlet S43 and the outlet portion 516 of U-shaped chamber 427. Dissipation hole 545 in this presently preferred embodiment is approximately 0.098 inches in diameter. Energy is stored in U-shaped chamber 427 during each oscillation cycle of snore sound. Dissipation hole 545 helps dissipate some of that energy to adjust the Q or quality factor (a measure of resonance) of the circuit. Thus, dissipation hole 545 dissipates the energy stored in each oscillation cycle of snore sound to make the Q of the U-shaped chamber 427 comparable to that of the CPAP device.

Figure 8:
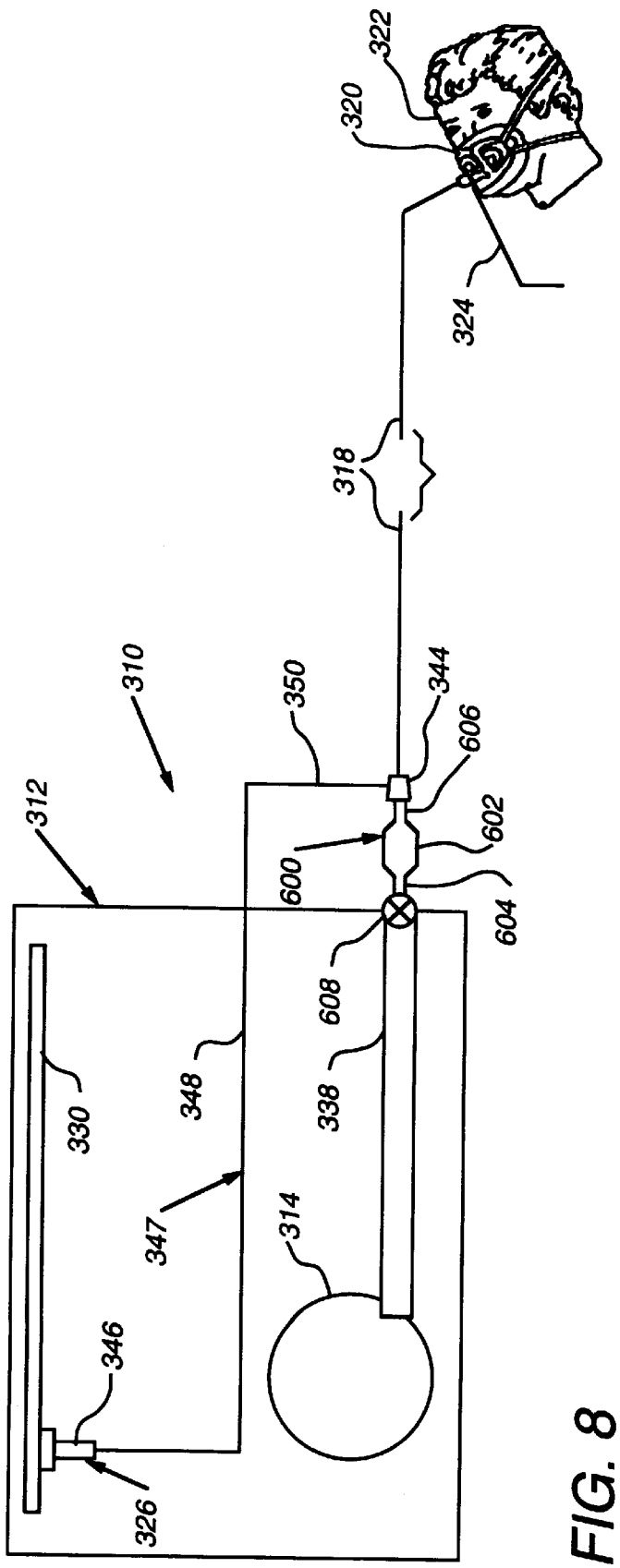
FIG. 8 is a view schematically illustrating the sleep apnea treatment apparatus in use with a preferred embodiment of a gas flow pressure filter of the present invention.
Figure 9:
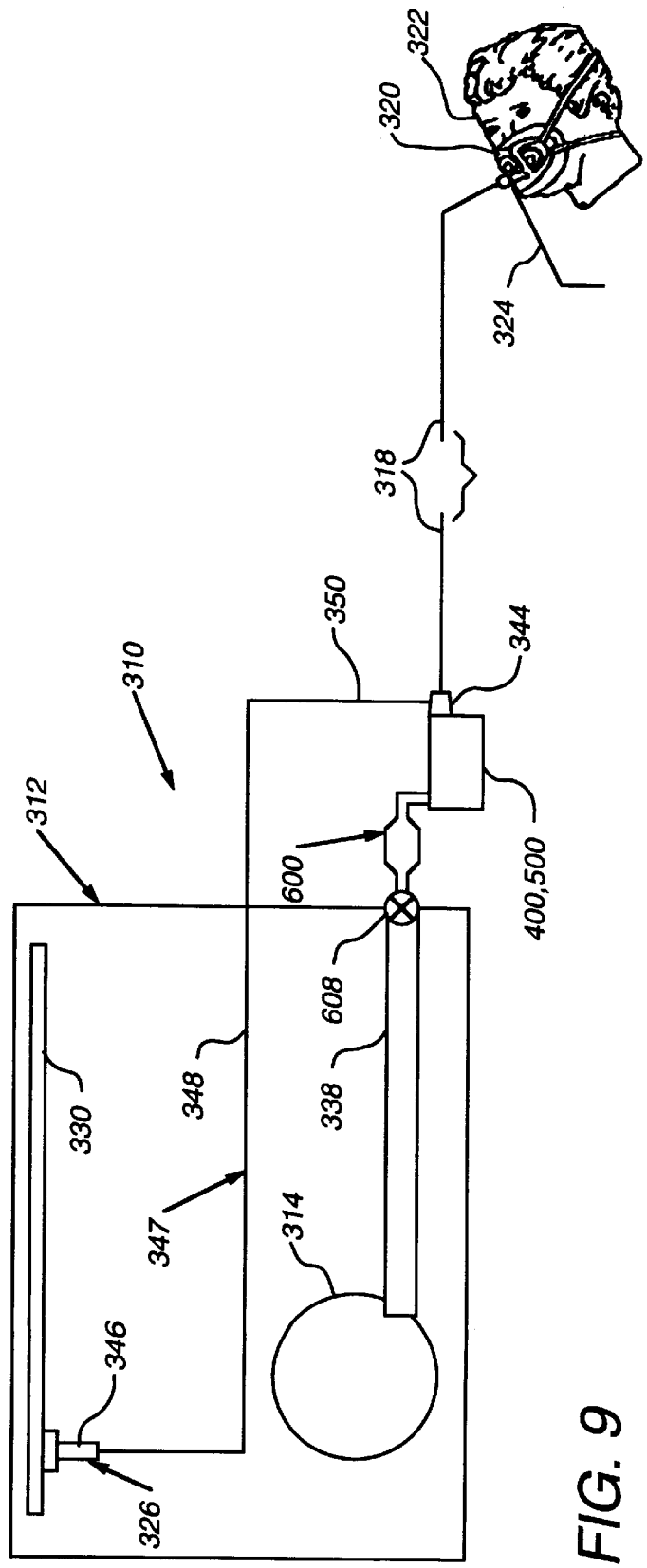
FIG. 9 is a view schematically illustrating the sleep apnea treatment apparatus in use with a humidifier and a gas flow pressure filter of the present invention.

Turning to FIG. 8, a sleep apnea treatment apparatus 310 according to the present invention is illustrated in combination with a gas flow pressure filter means 600 of the present invention. The currently preferred embodiment of the gas flow pressure filter 600 comprises a cylindrical chamber or bladder 602 having an inlet 604 and an outlet 606. The outlet of the gas flow generator device includes a valve 608 for controlling the gas flow from bellows 338 of the flow generator 314. Valve 608 contributes to the above-described pressure fluctuations. The gas flow pressure filter 600 is preferably connected in series with the gas flow stream with the inlet 604 of the gas flow pressure filter 600 connected to the outlet of the valve 608. The circuit coupler 344 is preferably attached at the outlet 606 of the gas flow pressure filter 600 or downstream thereof when used in combination with a humidifier 400, 500 (FIG. 9).

Figure 10:
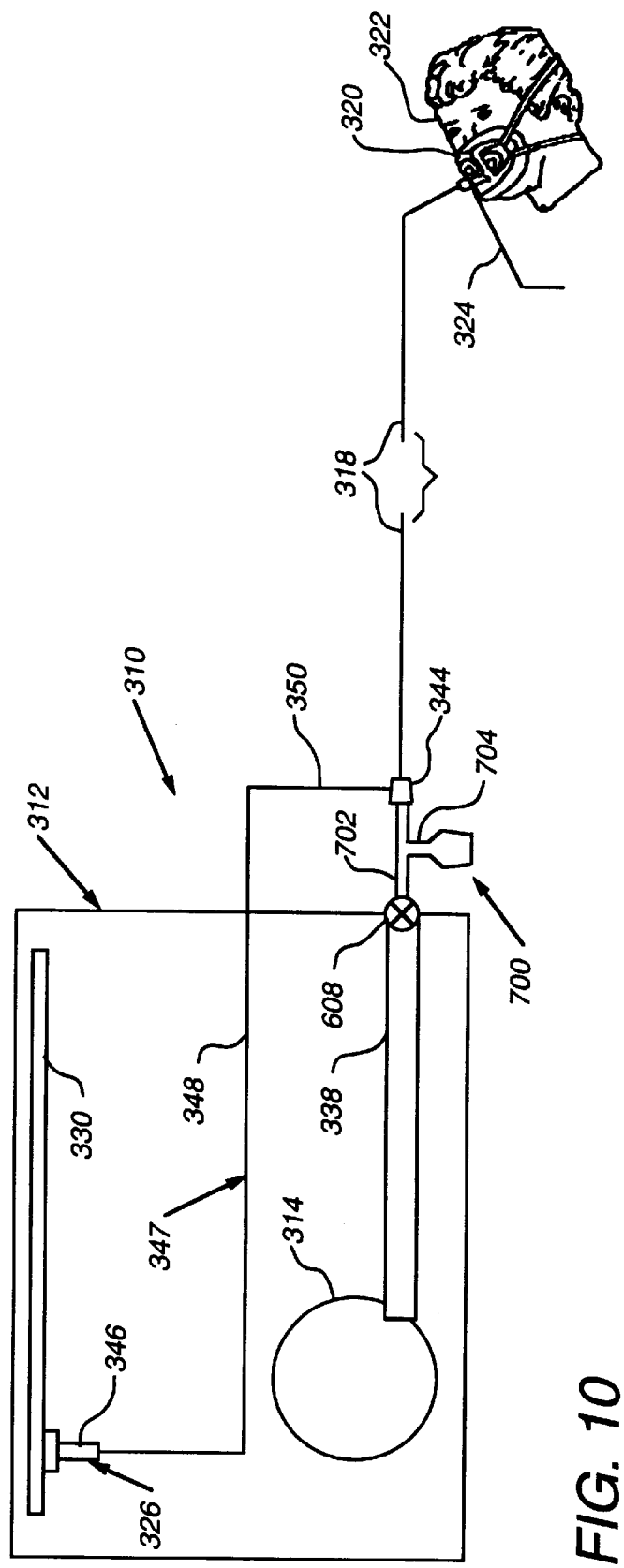
FIG. 10 is a view schematically illustrating the sleep apnea treatment apparatus in use with a gas flow pressure filter connected via a "T" coupling.

Alternatively as illustrated in FIG. 10, the gas flow pressure filter 700 may be connected via a "T" coupling 702 with the gas flow stream. In this embodiment, the bladder has a single inlet/outlet 704. In a further unillustrated embodiment, the gas flow pressure filter may be connected in parallel with the gas flow stream.

Figure 11:
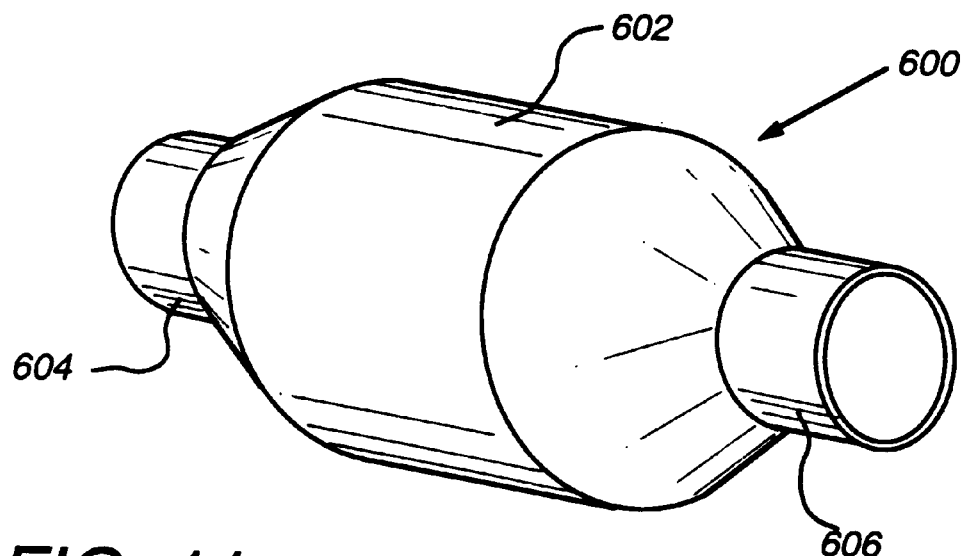
FIG. 11 is a perspective view of the preferred embodiment of the gas flow pressure filter in a pressurized state.
Figure 12:
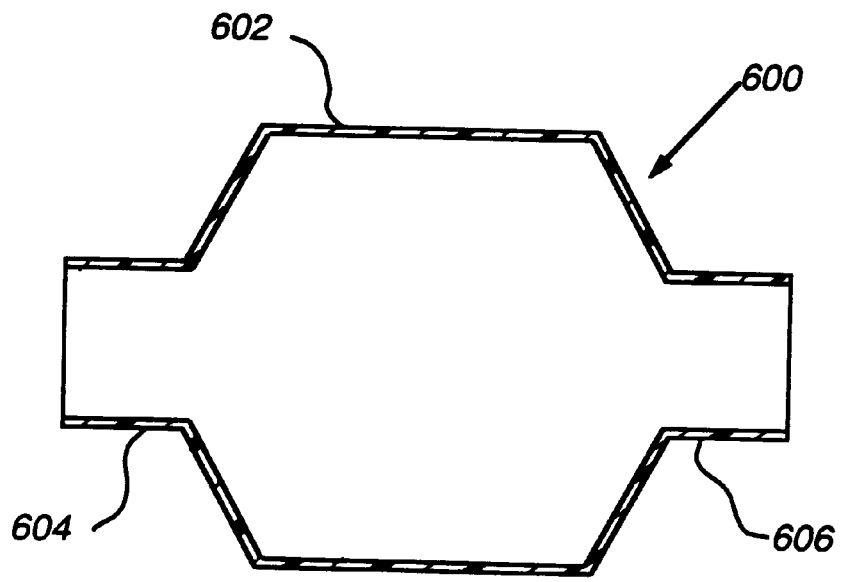
FIG. 12 is a cross-sectional view of the preferred embodiment of the gas flow pressure filter in a pressurized state.

The gas flow pressure filter 600 comprises a cylindrical bladder 602 fabricated from any highly elastic material such as urethane or latex. In the preferred embodiment, the bladder 602 is formed from a thin urethane sheet (see FIGS. 11 and 12). The urethane is heat sealed and die cut to give the appropriate shape. The cylindrical bladder 602 maintains its cylindrical shape as long as there is sufficient gas pressure within the gas flow pressure filter 600. Otherwise, without sufficient pressure, the bladder 602, will resemble a collapsed balloon due to its highly flexible construction. It should be apparent that the invention is not limited to a cylindrical shape and that other shapes are within the scope of the invention such as rectangular or convoluted bellows shapes. The urethane component also incorporates the inlet and outlet which are used to install the filter 600 into the circuit.

The incorporation of the gas flow pressure filter 600 allows for the extraction of pressure/flow fluctuations of interest via simple electronic techniques. The gas flow pressure filter 600 is simple to manufacture and adds little cost to the system. When used with the above-disclosed positive airway pressure device 310, patient snore sounds can be readily detected in a manner described hereinabove.

While the gas flow pressure filter 600, 700 has been illustrated as being positioned outside the device 312, it may be desirable to locate the filter 600, 700 within the device due to its highly flexible construction. Alternatively, the gas flow pressure filter may be positioned at any location along the gas flow stream. Under some conditions, it may be desirable to locate the gas flow pressure filter at the patient interface end of the first conduit means 318 when sensors are located there.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Apparatus for delivering pressurized gas to an airway of a patient, said apparatus comprising:

gas flow generator means for providing a gas flow;

gas flow pressure filter means connected to said gas flow generator means for absorbing excessive pressure fluctuations in said gas flow provided by said gas flow generator means;

patient interface means for sealingly communicating with an airway of a patient;

conduit means for delivery of said gas flow to an airway of such a patient, said conduit means having a first portion in communication with said gas flow pressure filter means and a second portion in communication with said patient interface means.

2. The apparatus of claim 1, wherein said gas flow pressure filter means includes a single inlet/outlet.

3. The apparatus of claim 2, further comprising a "T" coupling for coupling said gas flow pressure filter means to said gas flow generator means and said conduit means.

4. The apparatus of claim 1, wherein said gas flow pressure filter means comprises a compliant chamber.

5. The apparatus of claim 4, wherein said compliant chamber is cylindrical.

6. The apparatus of claim 5, wherein said compliant chamber is formed from a urethane sheet.

7. The apparatus of claim 1, further comprising a humidifier means coupled between said gas flow pressure filter means and said conduit means for moisturizing said flow of pressurized gas.

8. Apparatus for delivering pressurized gas to an airway of a patient, said apparatus comprising:

gas flow generator means for providing a gas flow;

a gas flow pressure filter means connected to said gas flow generator means for absorbing excessive pressure fluctuations in said gas flow provided by said gas flow generator means;

patient interface means for sealingly communicating with an airway of a patient;

conduit means for delivery of said gas flow to an airway of such a patient, said conduit means having a first portion in communication with said gas flow pressure filter means and a second portion in communication with said patient interface means;

sensor means in fluid communication with said conduit means and located substantially at said gas flow generator means for detecting conditions corresponding to breathing patterns of such a patient and for generating signals corresponding sound frequencies falling within a frequency range known to be associated with upper airway obstructions; and information processing means for receiving said signals and for controlling an output of said gas flow generator means responsive to said signals.

9. The apparatus of claim 8, wherein said gas flow pressure filter means includes a single inlet/outlet.

10. The apparatus of claim 9, further comprising a "T" coupling for coupling said gas flow pressure filter means to said gas flow generator means and said conduit means.

11. The apparatus of claim 8, wherein said gas flow pressure filter means comprises a compliant chamber.

12. The apparatus of claim 11, wherein said compliant chamber means is cylindrical.

13. The apparatus of claim 12, wherein said compliant chamber means is formed from a urethane sheet.

14. The apparatus of claim 8, further comprising a humidifier means coupled between said gas flow pressure filter and said conduit means for moisturizing said flow of pressurized gas.

15. Apparatus for delivering pressurized gas to an airway of a patient, said apparatus comprising:

gas flow generator means for providing a gas flow;

a gas flow pressure filter means connected to said gas flow generator means for absorbing excessive pressure fluctuations in said gas flow provided by said gas flow generator means;

patient interface means for sealingly communicating with an airway of a patient;

first conduit means for delivery of said gas flow to an airway of such a patient, said conduit means having a first portion in communication with said gas flow pressure filter means and a second portion in communication with said patient interface means;

sensor means in fluid communication with said conduit means for detecting conditions corresponding to breathing patterns of such a patient and generating signals corresponding to said conditions;

second conduit means for communicating said conditions to said sensor means, said second conduit means having a first portion communicating with said sensor means and a second portion communicating with said conduit means and being located substantially at said gas flow pressure filter means, said second conduit means being acoustically tuned to optimally transmit sound frequencies falling within a range which is known to be associated with upper airway obstructions; and information processing means for receiving said signals and for controlling an output of said gas flow generator means responsive to said signals.

16. The apparatus of claim 15, wherein said gas flow pressure filter means includes a single inlet/outlet.

17. The apparatus of claim 16, further comprising a "T" coupling for coupling said gas flow pressure filter means to said gas flow generator means and said conduit means.

18. The apparatus of claim 15, wherein said gas flow pressure filter means comprises a compliant chamber.

19. The apparatus of claim 18, wherein said compliant chamber means is cylindrical.

20. The apparatus of claim 19, wherein said compliant chamber means is formed from a urethane sheet.

21. The apparatus of claim 15, further comprising a humidifier means coupled between said gas flow pressure filter and said conduit means for moisturizing said flow of pressurized gas.

22. Apparatus for delivering pressurized gas to an airway of a patient, said apparatus comprising:

a gas flow generator;

a conduit operatively coupled to said gas flow generator for carrying a gas flow produced by said gas flow generator;

a patient interface operatively coupled to said conduit to communicate said gas flow carried by said conduit with an airway of a patient; and a gas flow pressure filter operatively coupled to at least one of said gas flow generator, said conduit, and said patient interface, said gas flow pressure filter being configured and arranged so as to absorb excessive pressure fluctuations in said gas flow provided by said gas flow generator.

23. The apparatus of claim 22, further comprising:

a sensor in fluid communication with said conduit to detect conditions corresponding to breathing patterns of such a patient and to generate signals corresponding to said conditions; and an information processor that receives said signals and controls an output of said gas flow generator responsive to said signals.

24. The apparatus of claim 23, further comprising a sensor conduit having a first portion communicating with said sensor and a second portion communicating with said conduit, said sensor conduit means being acoustically tuned to optimally transmit sound frequencies falling within a range which is known to be associated with upper airway obstructions.

* * * * *